(12) United States Patent
Volkodav et al.

(10) Patent No.: US 10,926,070 B2
(45) Date of Patent: Feb. 23, 2021

(54) SHUNT SYSTEMS AND METHODS FOR REMOVING EXCESS CEREBROSPINAL FLUID

(71) Applicant: KOUCKY & VOLKODAV LLC, Carmel Valley, CA (US)

(72) Inventors: Oleg Volkodav, Simferopol (UA); Irina Koucky, Carmel Valley, CA (US)

(73) Assignee: KOUCKY & VOLKODAV LLC, Carmel Valley, CA (US)

( * ) Notice: Subject to any disclaimer, the term of this patent is extended or adjusted under 35 U.S.C. 154(b) by 493 days.

(21) Appl. No.: 15/874,264

(22) Filed: Jan. 18, 2018

(65) Prior Publication Data

US 2018/0140811 A1 May 24, 2018

Related U.S. Application Data

(62) Division of application No. 15/698,278, filed on Sep. 7, 2017, now Pat. No. 10,052,463.

(60) Provisional application No. 62/393,563, filed on Sep. 12, 2016.

(51) Int. Cl.
*A61M 27/00* (2006.01)
*A61M 39/02* (2006.01)

(52) U.S. Cl.
CPC .......... *A61M 27/006* (2013.01); *A61M 39/02* (2013.01); *A61M 2202/0464* (2013.01); *A61M 2210/02* (2013.01); *A61M 2210/0693* (2013.01)

(58) Field of Classification Search
CPC ......................... A61M 27/006; A61M 27/002
See application file for complete search history.

(56) References Cited

U.S. PATENT DOCUMENTS

| | | | |
|---|---|---|---|
| 3,111,125 | A | 11/1963 | Schulte |
| 3,288,142 | A | 11/1966 | Hakim |
| 3,527,226 | A | 9/1970 | Hakim et al. |
| 3,595,240 | A | 7/1971 | Mishler |
| 3,886,948 | A | 6/1975 | Hakim |
| 3,985,140 | A | 10/1976 | Harris |
| 4,464,168 | A | 8/1984 | Redmond et al. |
| 4,551,128 | A | 11/1985 | Hakim et al. |
| 5,069,663 | A | 12/1991 | Sussman |
| 5,637,083 | A | 6/1997 | Bertrand et al. |

(Continued)

FOREIGN PATENT DOCUMENTS

WO WO 2016/132930 A1 8/2016

OTHER PUBLICATIONS

File History from U.S. Appl. No. 15/698,278.
(Continued)

*Primary Examiner* — Leslie R Deak
(74) *Attorney, Agent, or Firm* — Knobbe, Martens, Olson & Bear, LLP (57) ABSTRACT

A shunt device for directing fluid from a human head, and methods thereof are provided herein. The device can be mounted at a skull and include a first catheter that extends into a portion of the head such as a lateral ventricle. The first catheter can covey fluid through, and past a valve to a shunt body. The shunt body can include openings, allowing the fluid to reenter the head, for example at the subarachnoid space. The shunt body can also include other openings that can be associated with a second catheter. Fluid can thus also be conveyed out of the body or to a subgaleal pocket.

11 Claims, 7 Drawing Sheets

(56) References Cited

U.S. PATENT DOCUMENTS

| | | |
|---|---|---|
| 5,662,600 A | 9/1997 | Watson et al. |
| 7,513,883 B2 | 4/2009 | Glenn |
| 9,033,909 B2 | 5/2015 | Aihara |
| 10,052,463 B2 * | 8/2018 | Volkodav ............ A61M 27/006 |
| 2004/0267187 A1 | 12/2004 | Rosenberg |
| 2005/0277865 A1 | 12/2005 | Gharib et al. |
| 2006/0004317 A1 | 1/2006 | Mauge et al. |
| 2008/0125690 A1 | 5/2008 | Delaporte |
| 2012/0046595 A1 | 2/2012 | Wilson et al. |
| 2012/0232462 A1 | 9/2012 | Miethke |
| 2015/0297874 A1 | 10/2015 | East et al. |

OTHER PUBLICATIONS

International Search Report and Written Opinion dated Dec. 4, 2017 for Application No. PCT/US2017/050789.

Office Action dated Nov. 25, 2020 in Chinese Patent Application No. 201780069367.0.

Office Action dated Nov. 30, 2020 in Russian Patent Application No. 2019106703.

\* cited by examiner

SHUNT SYSTEMS AND METHODS FOR REMOVING EXCESS CEREBROSPINAL FLUID

INCORPORATION BY REFERENCE TO ANY PRIORITY APPLICATIONS

This application claims priority benefit under 35 U.S.C. § 119(e) to U.S. patent application Ser. No. 15/698,278 filed 7 Sep. 2017 entitled "SHUNT SYSTEMS AND METHODS FOR REMOVING EXCESS CEREBROSPINAL FLUID", which is a divisional application, and U.S. Provisional Patent Application Ser. No. 62/393,563 filed 12 Sep. 2016 entitled "STENT SYSTEM FOR REMOVING EXCESS CEREBROSPINAL FLUID", the entirety of each hereby expressly incorporated by reference herein.

BACKGROUND

Field

The embodiments herein relate generally to shunt systems, particularly for removing excess cerebrospinal fluid.

Description of the Related Art

Shunt systems can be used in a variety of circumstances. For example, a patient with hydrocephalus experiences excess cerebrospinal fluid accumulating in the brain and causing high intracranial pressure. Such accumulations can occur when the natural movement of cerebrospinal fluid is blocked or excessive pressure results from injury or other causes. A shunt system can be used to allow the fluid to flow out of the impacted region, thus reducing the intracranial pressure.

SUMMARY

The shunt systems described herein can be used in the human brain to treat hydrocephalus, and are described in that context herein. However, the shunt systems can also be used in other contexts. Similarly, although the shunt systems are described as conveying cerebrospinal fluid, they can also be used to convey other fluids such as blood, or medical treatments, and they may have veterinary or other commercial uses.

Figure 1:
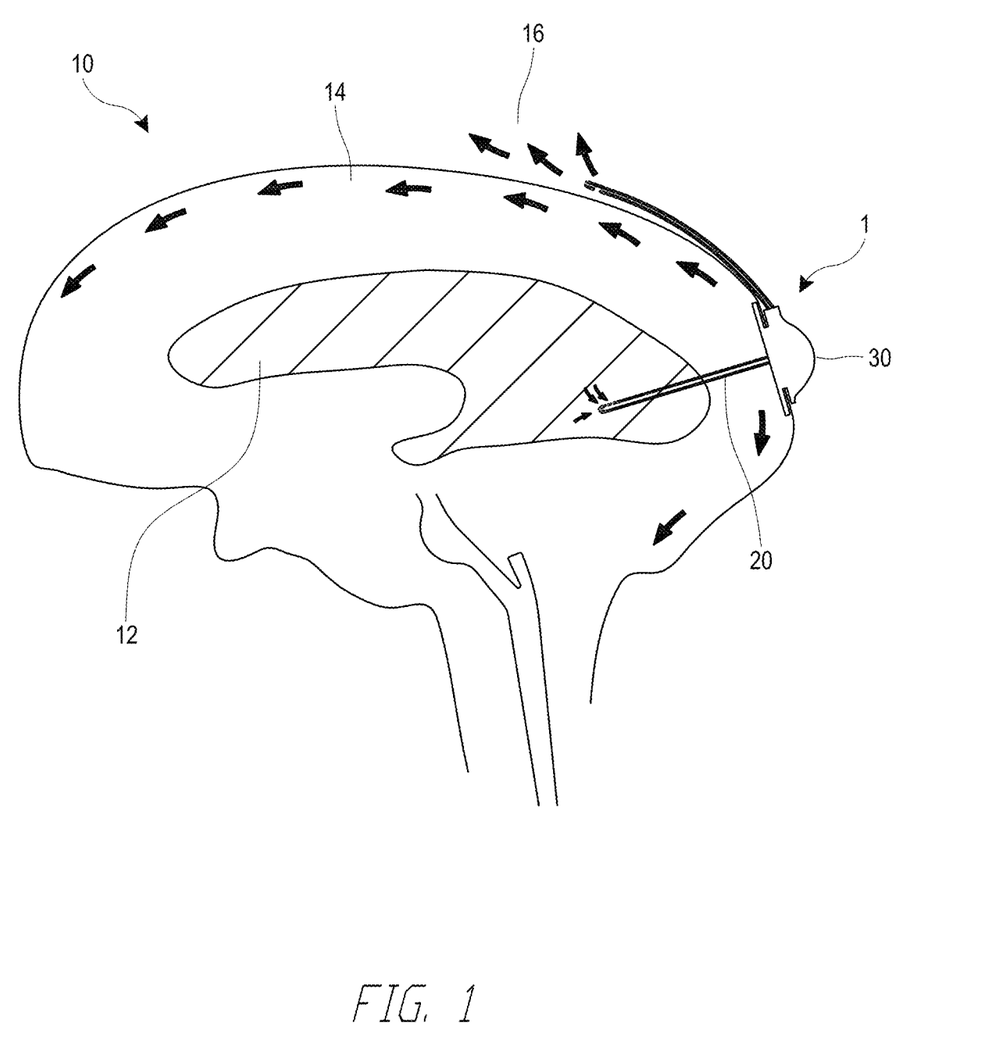
FIG. 1 is a cross-sectional view of a human head with an implanted shunt device.

As shown in FIG. 1, a shunt 1 can be implanted into a human head 10 (or more specifically, a human brain). The shunt 1 can include a first catheter 20 extending into a lateral ventricle 12, although the shunt can be used in other contexts. The first catheter 20 can thus conduct fluids, such as cerebrospinal fluid, from the ventricle 12 to a shunt body 30. The shunt body 30 can then allow this fluid to either be conveyed into the subarachnoid space 14 or be diverted to a subgaleal pocket 16. The subgaleal pocket 16 is typically bounded between the skull and the skin of the head, the skin not shown in FIG. 1. Cerebrospinal fluid that is reintroduced into the subarachnoid space 14 can then recirculate throughout the head 10 (within the skull), promoting natural flows of the cerebrospinal fluid. Excess fluid can also exit to the subgaleal pocket 16, from which it can be reabsorbed into the body's subgaleal pocket or be removed from the body with a needle or other device.

The shunt 1 can have two flanges integrated into the design to secure the device in a hole in the skull. The reliable fixation can seal the hole from any leakage.

The present application contemplates various shunt devices that can perform these functions. For example a shunt device for removing excess cerebrospinal fluid in a human head, the shunt device can include a first catheter, a shunt body, and a second catheter. The first catheter can include a first lumen and at least one first catheter opening substantially at a distal end of the first catheter. The shunt body can be attached to the first catheter at a proximal end of the first catheter. The shunt body can also include a chamber in communication with the first lumen, a mount, and at least one chamber opening. The mount can be configured to position the shunt body in a human skull, the mount dividing the shunt body into an intracranial portion and an extracranial portion when positioned in the skull. The first catheter can extend from the intracranial portion at the proximal end of the first catheter. The at least one chamber opening can be on the intracranial portion and in communication with the chamber such that fluid entering the chamber from the first catheter can simultaneously exit the chamber through the at least one chamber opening. The second catheter can be attached to the shunt body in the extracranial portion. The second catheter can also include a second lumen in communication with the chamber such that fluid entering the chamber from the first catheter can exit the chamber through the second catheter.

In a further, embodiment, a shunt device for removing excess cerebrospinal fluid in a human head can include a first catheter and a shunt body. The first catheter can include a first lumen and at least one first catheter opening substantially at a distal end of the first catheter. The shunt body can attach to the first catheter at a proximal end, and can include a chamber in communication with the first lumen, one or more flanges, at least one first chamber opening, and at least one second chamber opening. The one or more flanges can be configured to mount the shunt body to a human skull, dividing the shunt body into an intracranial portion and an extracranial portion when mounted to the skull. The first catheter can also extend from the intracranial portion at the proximal end of the first catheter. The at least one first chamber opening can be in the intracranial portion and in communication with the chamber such that fluid entering the chamber from the first catheter can simultaneously exit the chamber through the at least one first chamber opening. The at least one second chamber opening can be in the extracranial portion and in communication with the chamber such that fluid entering the chamber from the first catheter can exit the chamber through the at least one second chamber opening.

In a further embodiment, a method of removing excess cerebrospinal fluid can be provided. A hole in a skull can be created. A probe can be inserted into a hole in a catheter of a shunt device, and the first catheter can be pulled into a desired position within the skull using the probe, such that cerebrospinal fluid can flow through the first catheter into the shunt device. The shunt body can then mount into a hole in the skull while the first catheter is in the desired position.

In a further embodiment, a method of removing excess cerebrospinal fluid can be provided. Cerebrospinal fluid from an intracranial region can be received, and conveyed to a chamber mounted at a skull. The fluid can then be conveyed from the chamber to a subarachnoid space of the brain when pressure in the subarachnoid space is not excessive. The fluid can also be conveyed from the chamber to a subgaleal pocket when the pressure in the subarachnoid space is excessive. The method can be performed continuously over at least a week without surgical interference inside the skull.

BRIEF DESCRIPTION OF THE DRAWINGS

Further objects, features and advantages will become apparent from the following detailed description taken in conjunction with the accompanying figures showing illustrative embodiments, in which.

DETAILED DESCRIPTION OF THE PREFERRED EMBODIMENTS

As shown in FIG. 1, the shunt device 1 can be used to access a region of a head 10 (such as a lateral ventricle 12) and convey fluid (such as cerebrospinal fluid) from that region to another region of the head (such as the subarachnoid space 14) or outside of the head (such as to a subgaleal pocket 16). However, it will be understood that the device can be used in other regions of a human body (including pre-mature newborns, mature newborns, children, and adults), or a non-human body (with dimensions adjusted accordingly). For example, the device can also be used on other animals such as dogs, cats, cows, horses, sheep, and other pets or livestock (with dimensions adjusted accordingly). Further, the device can direct cerebrospinal fluid from other regions in the brain to other parts of the body, such as directing liquid from benign intracranial cysts, and providing a second stage fluid outflow to the peritoneal cavity after integration with a traditional peritoneal shunt.

The device can also be used to facilitate the purification and sanitation of blood, such as in the context of post-hemorrhagic hydrocephalus in infants, porencephalus, and post-hemorrhagic cysts. The device can also be used in the context of post-hemorrhagic arachnoiditis prevention or treatment, such as for the infusion of saline solutions or physiological solutions. The device can also be used to direct other fluids, such as blood between different regions of the body.

Figure 2:
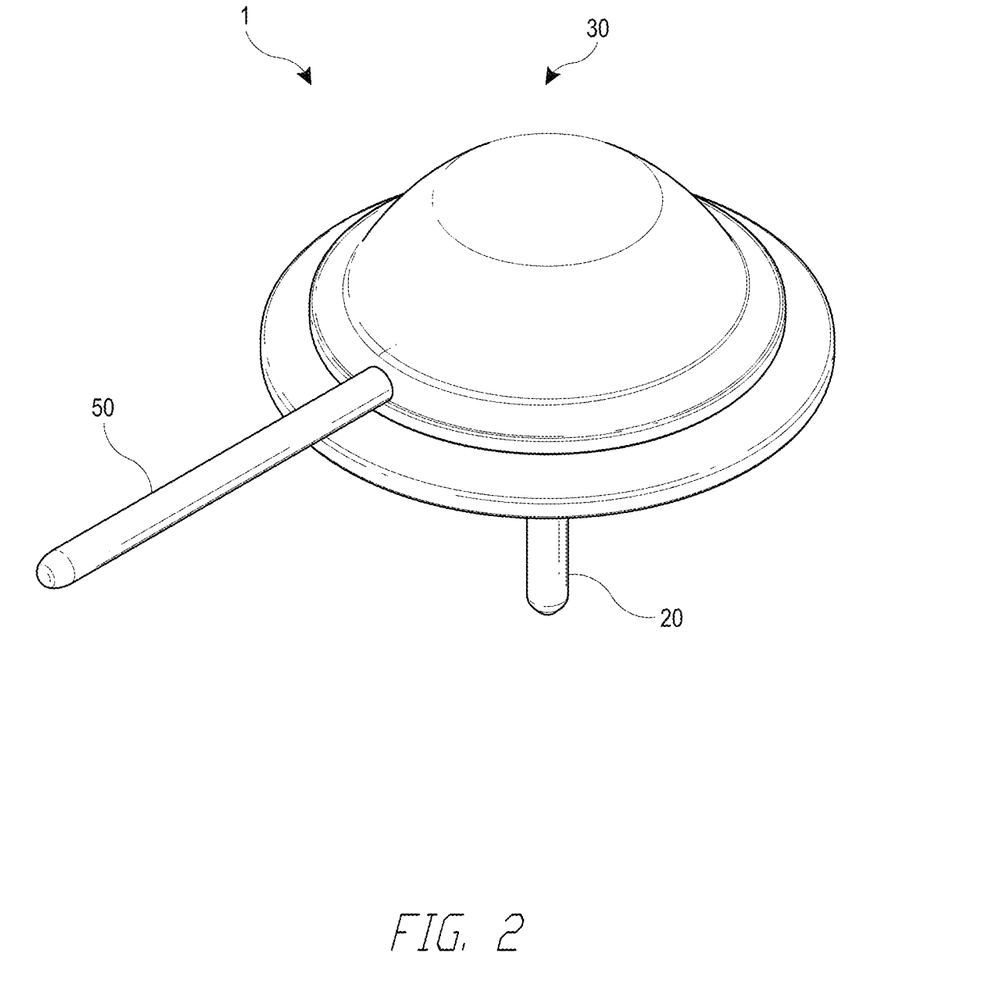
FIG. 2 is a perspective view of a shunt device.
Figure 3:
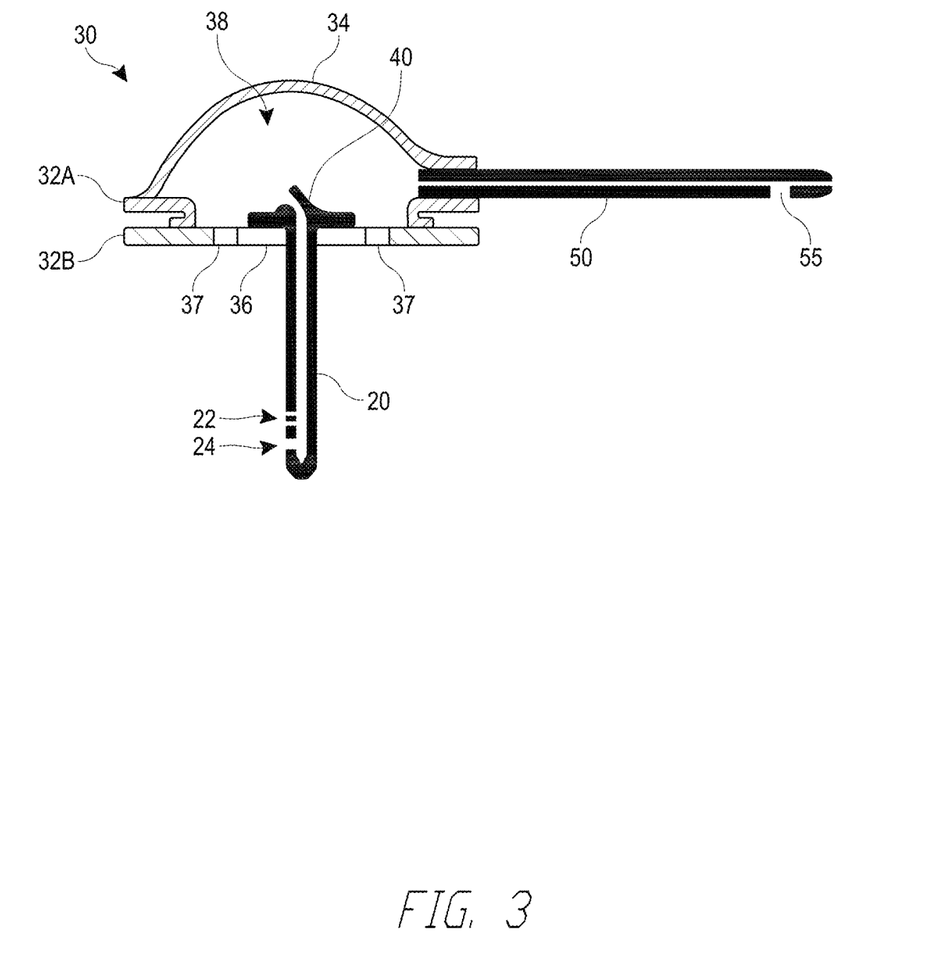
FIG. 3 is a cross-sectional view of the shunt device of FIG. 2.

As more clearly shown in FIGS. 2 and 3, the shunt device 1 can include a shunt body 30 with a first catheter 20 extending from the shunt body on a lower side of the device and a second catheter 50 extending from the shunt body on a lateral side of the device (extending generally along the exterior of the head/skull). As discussed further herein (and depicted, for example, in FIG. 1), the shunt device 1 can be mounted within a skull, such that the "lower" side depicted in the figures can be called an intracranial side, or patient-facing side. Similarly, a "lateral" or "upper" side of the device can be called an extracranial side of the device, or outer-facing side. However, it will be understood that the device can also be provided in other orientations.

The shunt device 1 can be inserted into a hole in the skull, and be self-sealing inside the hole with flanges (further described below). As also further described below, the shunt device 1 can include openings that allow excess fluid to be directed back down, into the skull (such as into a subarachnoid space).

The first catheter 20 can extend into the head 10, particularly a lateral ventricle 12, although it will be clear that it could also extend into other parts of the head such as into a benign intracranial cyst. The first catheter can be formed from silicone (such as medical grade silicone), and be generally flexible to allow a physician to position it in a variety of locations and orientations. The first catheter can have a width of at least 1 mm, at least 1.5 mm, or at least 2 mm, and can also be less than 3 mm, less than 4 mm, or less than 5 mm. The first catheter can also have a length of at least 30 mm, at least 40 mm, or at least 50 mm, and less than 70 mm, less than 80 mm, or less than 100 mm. Dimensions can be further modified, as appropriate for the intended use. The first catheter can have a length sufficient to extend from a trepanned hole in the skull to a lateral ventricle. The first catheter can also have a lumen with a size of at least 0.5 mm, 1 mm, or 2 mm, and optionally also less than 3 mm or less than 2 mm. These sizes can be sufficient to transport cerebrospinal fluid under most conditions.

As best shown in FIG. 3, the first catheter 20 can include at least one opening 22 substantially at an end distal from the shunt body 30. FIG. 3 shows two openings 22, although the catheter can optionally have one opening, more than two openings, four openings, or more than four openings. The openings 22 can be substantially at the distal end of the first catheter 20 to allow the conveyance of fluid through nearly the entire length of the first catheter. The openings 22 can have a size of at least 0.1 mm, 0.2 mm, or 0.3 mm, sufficient to transport cerebrospinal fluid. The openings 22 can also be sufficiently small to avoid the uptake of larger bodies such as blood clots, or choroid plexus, with a size no larger than 0.5 mm. Similarly, the distal end of the lumen of the first catheter 20 can optionally be axially closed to prevent the uptake of large bodies that might obstruct the shunt device 1. The openings 22 can optionally be disposed laterally, on a side of the first catheter 20, near the distal end, as shown in FIG. 3.

The first catheter 20 can also include a guide opening 24. The guide opening 24 can be used, as further described below, to guide the first catheter 20 into a desired position, such as within a lateral ventricle 12 or a benign intracranial cyst. As shown, the guide opening 24 can optionally be provided below (or distal) from the other openings 22. Further, the guide opening 24 can optionally have a larger size, to receive a guide or probe further described below, or can be the same size as the other openings 22.

The first catheter 20 can extend, from its distal end, upwards to its proximal end where it connects to the shunt body 30. The shunt device 1 can also optionally include a valve 40 to allow flow from the first catheter 20 to the shunt body 30, but substantially hinder flow from the shunt body 30 to the first catheter 20. The valve 40 can be a self-closing check valve, a ball check valve, a diaphragm check valve, a petal valve, a swing check valve, or other types of valves. Although the valve 40 in FIG. 3 is depicted as a part of the first catheter 20, it can also be a part of the shunt body 30 (for example, a part of the shunt body floor 36), or be a separate piece connecting the shunt body and the first catheter. The valve 40 can be formed from medical silicone. The fluid pressure required to open the valve 40 to allow flow into the shunt device 1 (such as from the first catheter 20 to the chamber 38) can be greater than 10 mm of water, or greater than 20 mm of water. For example, the pressure can be adapted to the smallest physiological age-related intracranial pressure in people such as premature newborns or adults. In other applications, other pressures can be used.

The lumen of the first catheter 20 can be in communication with the interior of the shunt body 30 (for example, through the optional valve 40). As shown in FIG. 3, the shunt body 30 can define a chamber 38. The chamber 38 can be bounded by a substantially planar floor 36 on an intracranial side of the shunt body 30. The chamber 38 can be also be bounded by a dome 34 on an upper, extracranial side of the shunt body 30. As shown in FIG. 3, the shunt body 30 can be formed primarily by two pieces (the dome 34 and the floor 36) being joined together. However, in other embodiments portions of the shunt body 30 can be formed by a variety of other pieces, such as with additional side walls (further discussed below, regarding FIG. 7).

Figure 4:
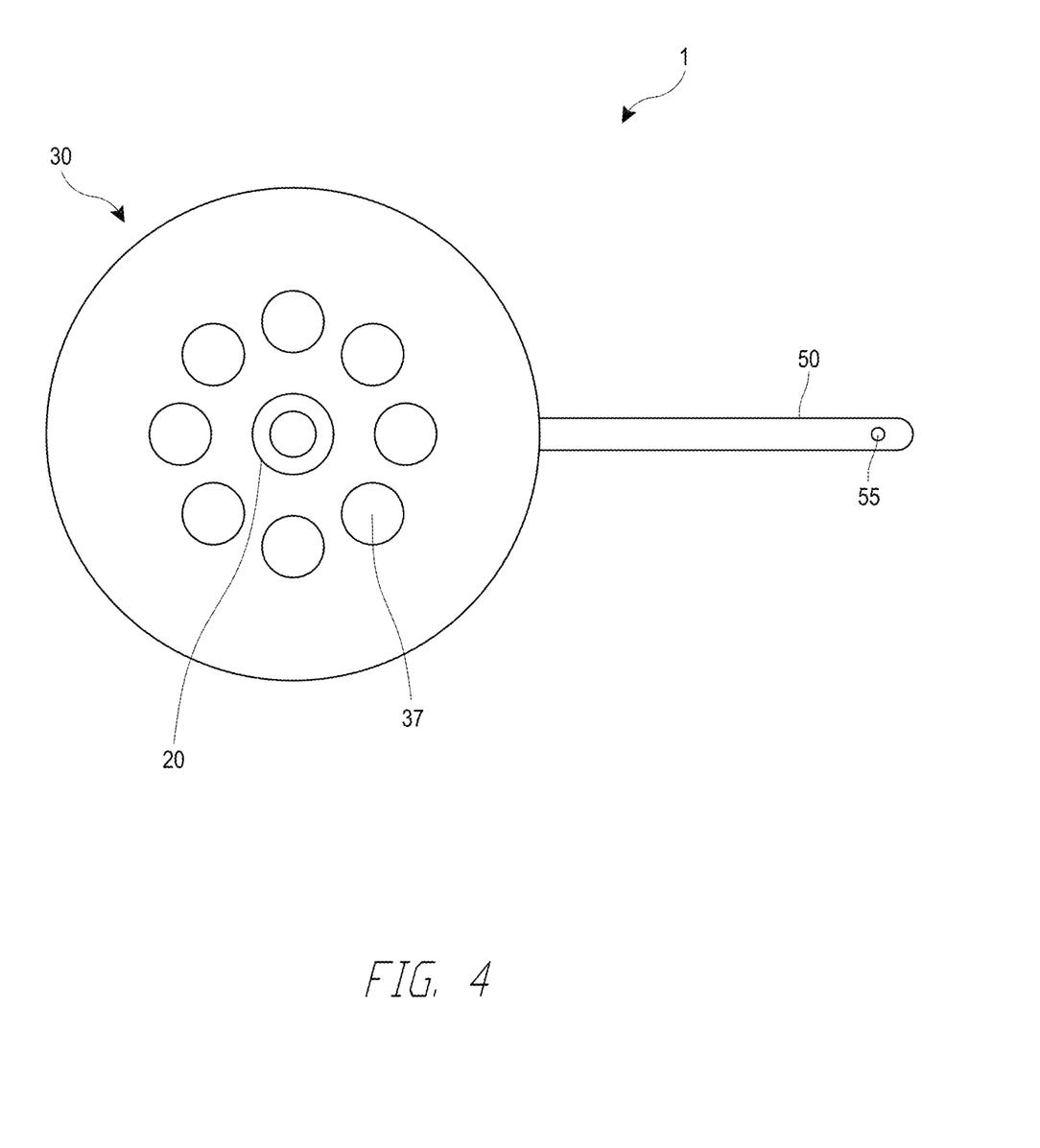
FIG. 4 is a bottom view of the shunt device of FIG. 2.
Figure 5:
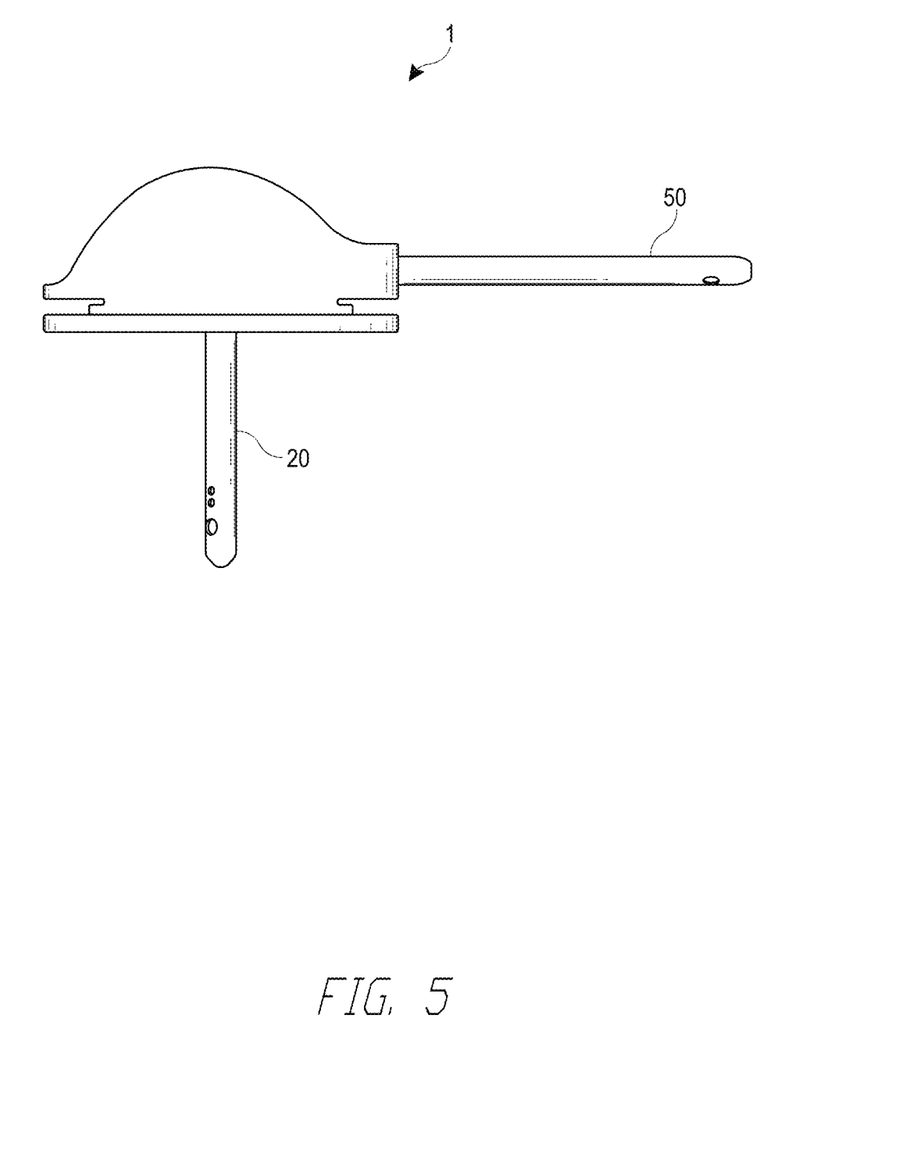
FIG. 5 is a side view of the shunt device of FIG. 2.

Further, as depicted in FIGS. 2, 3, and 4, the shunt body 30 can have a generally circular shape in a plane, such as a plane defined by the floor 36, a plane generally perpendicular to the first catheter 20, a plane parallel to the skull or a surface of the body, or a plane defined by one or more flanges 32. As shown in FIG. 3, the shunt body 30 can include two flanges 32A and 32B. The flanges 32A, 32B can extend around a perimeter of the shunt body 30. At least one of the flanges 32A, 32B can be defined by the shunt body floor 36. Similarly, at least one of the flanges 32A, 32B can be defined by the shunt body dome 34. As depicted in FIG. 3, the lower flange 32B can be defined by the floor 36 and the upper flange 32A can be defined by the dome 34. However, in other embodiments one of the floor 36 or the dome 34 may define two flanges.

The flanges 32A, 32B can be configured to mount the shunt body 30 within a patient's body. For example, the flanges 32 can be configured to receive the edges of a trepanned burr hole in a skull, with the lower flange 32B being within the arachnoid meninx and the upper flange 32A being straightened on the bone edges of the trepanation. The flanges 32 can be spaced apart approximately 4.5 mm, between 4 mm and 5 mm, or a skull width. Further, the flanges 32 can outwardly extend at least 4 mm from the rest of the shunt body 30. The flanges can also be configured to form a seal between the upper and lower sides of the shunt body 30 when mounted. For example, the flanges 32 can extend about the entire perimeter of the shunt body 30 on at least one side, or on both the upper and lower sides.

The lower portion of the shunt body 30 (such as the floor 36) can include one or more chamber openings 37, as best shown in FIG. 4. The chamber openings 37 allow flow of fluid within the chamber 38 out of the shunt body 30, downward (for example, toward the subarachnoid space). Thus, when the shunt body 30 is implanted within a skull, as discussed above, the fluid can flow from the chamber 38 into the head. As shown, eight chamber openings 37 can be provided, although other numbers of openings are also possible. The size of each opening can optionally be at least 1 mm or at least 2 mm in diameter, or a size large enough to allow larger bodies that may enter the first catheter (such as clots and fibrin) to exit the chamber 38. The sum of the areas of each opening can optionally be at least 10 mm squared or 20 mm squared. Further, the openings 37 can be positioned to allow fluid to flow through the openings from the chamber 38 into the subarachnoid space.

The upper portion of the shunt body 30 can define a dome 34. The upper portion of the shunt body 30 can provide space for the chamber 38, and thus can optionally have other non-dome shapes. The dome 34 (or at least some of the upper portion) can be formed of a material that can be easily penetrated by a needle (such as silicone), such that the chamber 38 can be accessed, as further discussed below. The dome 34 can be made of a flexible material, such that it can be pumped to facilitate the flow of fluids through the shunt device 1. For example, compressing the dome 34 can force fluid (and other particles that might clog the device) out through the second catheter 50 or the openings 37. Similarly, releasing the dome 34 can create a suction effect, bringing similar particles and fluid up through the first catheter 20.

The shunt body 30 can also include an opening for receiving a second catheter 50, such that the lumen of the second catheter is in communication with the chamber 38. As depicted, the chamber 38 can be disposed in the upper portion of the shunt body 30, above the flanges 32. Thus, when implanted in a skull, the second catheter can extend on an extracranial side of the device, such that fluid from inside the head (such as inside the lateral ventricles and subarachnoid space) can flow from the head, through the first catheter 20 to the chamber 38, and then out of the head through the second catheter 50. As shown in FIG. 3, the second catheter 50 can have a proximal opening at the chamber 38, and two distal openings 55, both axially at an opposite end from the chamber 38 and laterally, along a side of the second catheter generally near the distal end. However, in other embodiments the second catheter 50 can be mounted differently, or have different openings. For example, in some embodiments the second catheter 50 can communicate with the chamber 38 from above, instead of from the side. Similarly, the second catheter 50 can optionally only have an axial opening at the distal end or only have a lateral opening at the distal end. The second catheter 50 can optionally have a size, shape, and material generally similar to those options possible for the first catheter 20.

Figure 6:
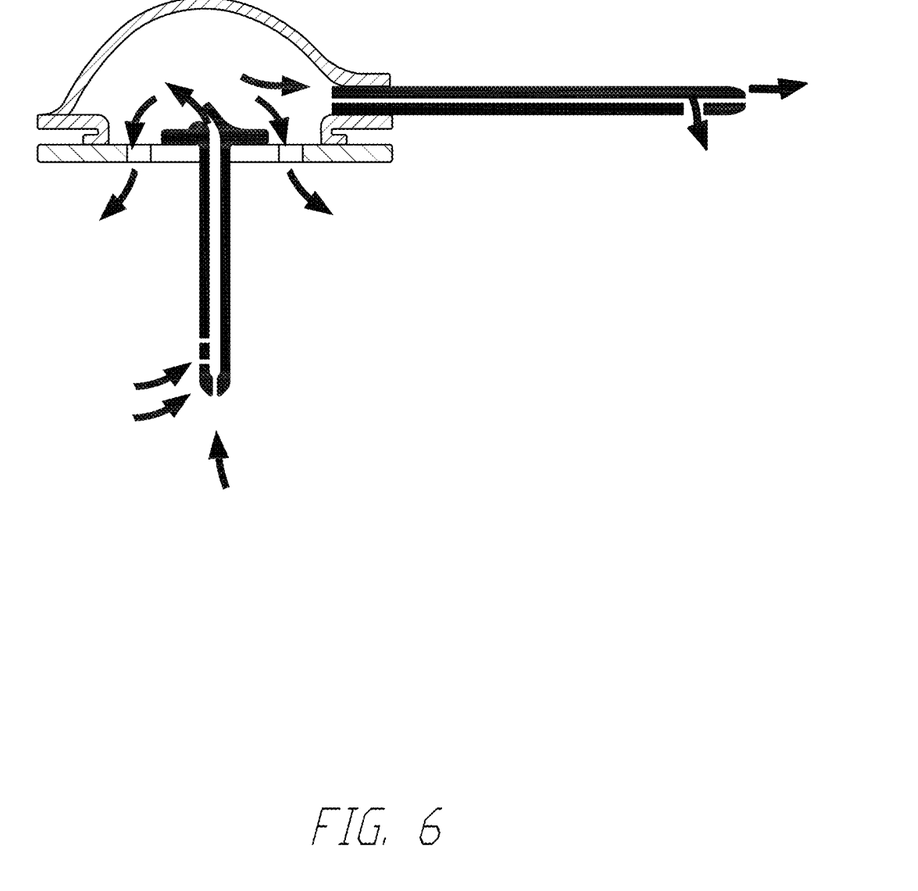
FIG. 6 is a cross-sectional view of the shunt device of FIG. 2, indicating directions of flow.

FIG. 6 depicts various ways fluid can be conveyed through the shunt device 1. As shown, fluid can be received from an intracranial region, through the first catheter 20. This fluid can then be conveyed, for example through the valve 40, into the chamber 38. From the chamber 38, the fluid can either be conveyed back downward through the chamber openings 37, or out through the second catheter 50. The flow's primary direction (through the chamber openings 37 into the subarachnoid space or the second catheter 50 to the subgaleal pocket) can be affected by a variety of factors including the size, shape, and orientation of the openings, fluid pressure at their outlets, and other factors. In some embodiments, the chamber openings 37 can define a generally larger area than the lumen of the second catheter 50, such that fluid from the chamber predominantly flows through the chamber openings absent a countervailing pressure.

Figure 7:
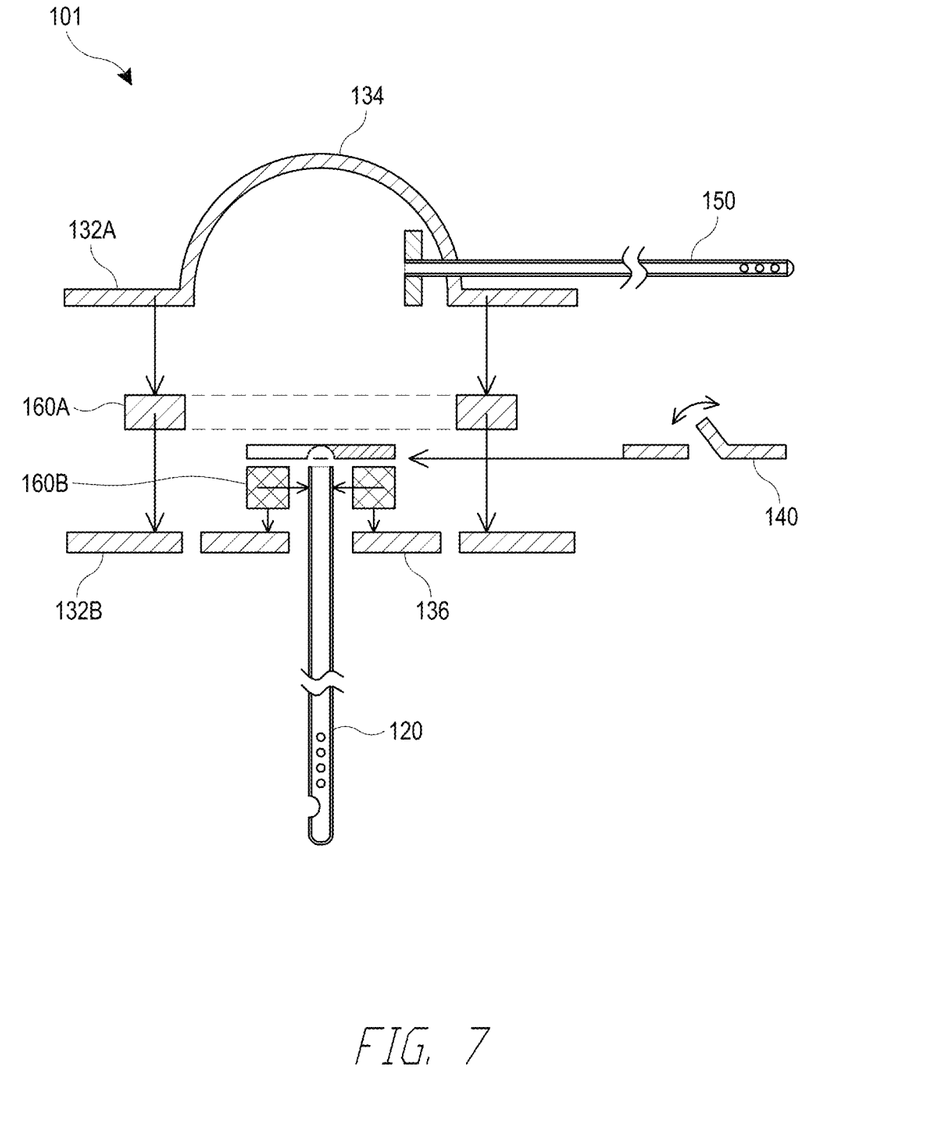
FIG. 7 is a cross-sectional and exploded view of a shunt device.

The shunt device 1 can be produced in a variety of ways. In some embodiments it can be 3D printed as a single piece shunt body 30, with the catheters 20, 50 attached separately. The valve 40 can be 3D printed with the body 30, or attached along with the first catheter 20. In other embodiments, the shunt device 1 can be assembled from a larger number of parts that can be welded, glued, or otherwise combined. FIG. 7 depicts an exploded view of a shunt device 101, substantially similar to the shunt device 1, but assembled from a larger number of parts, with similar parts having a corresponding reference number (increased by 100). The shunt device 101 can use additional walls 160A, 160B to provide space between flanges 132A, 132B, and between the valve 140 and the floor 136. Other variations on the manufacture of the shunt device 1 are also possible, such as by 3D printing other combinations of the components together as one piece. The components of the shunt body 30 can be formed from a variety of materials such as silicone.

After production, the shunt device 1 can optionally be inserted into a sterilized packaging. In some embodiments, the packaging can also include instructions for the use of the device, as further described below.

For implantation of the shunt device 1 into a patient, a burr hole in the skull can be made, generally matching the shape of the shunt body 30 at a mount such as between the flanges 32. The first catheter 20 can then be guided into a desired region of the head, such as a lateral ventricle 12. The first catheter 20 can be guided by an elongated, blunt probe that inserts into the guide opening 24. Once inserted into the guide opening 24, advancing the probe into the ventricle will similarly pull the first catheter 20 into the same location. The probe can then be pulled back, exiting the guide opening 24 while leaving the first catheter 20 behind. Cerebrospinal fluid from that location can then be conveyed through the first catheter 20.

The shunt body 30, attached to the first catheter 20, can then be mounted into the hole in the skull. When the flanges 32 are flexible, the shunt body 30 can be snapped into place within the hole, the skull disposed between the flanges. Further, if the hole and the shunt body 30 match sufficiently in size and shape then the shunt body 30 can also seal the hole, preventing any flow of fluid through the hole except through the shunt device 1.

The second catheter 50, attached to the shunt body 30, can then be advanced into a desired position outside the skull, but beneath the skin. Fluid flowing through the second catheter 50 from the shunt body 30 can then be collected in a subgaleal pocket. Alternatively, in some embodiments the second catheter 50 can direct fluid to a location outside the body, or other locations in the body.

After implantation, the shunt device 1 can receive cerebrospinal fluid from an interior of the head. This fluid can enter the chamber 38, substantially at the skull. Some of this fluid can then be conveyed back into the subarachnoid space of the head, into a subgaleal pocket, or another location. The flow can be determined by a pressure in the subarachnoid space, as well as a pressure in the subgaleal pocket. Because the device is implanted in the patient, this conveying of fluid can proceed continuously over extended periods of time, such as a week, a month, a year, or longer. No additional surgical interference inside the skull is necessary to continue this conveying of fluid.

Occasionally, there may be an excessive build-up of fluid in the subgaleal pocket that should be removed. In this situation, a needle can access the pocket and remove the fluid.

At other times, it may be determined that larger bodies have entered the shunt device 1. In this situation, a needle can optionally be used to penetrate the dome 34 (or the upper side of the shunt device 1) and inject fluid into the chamber 38 at a pressure sufficient to flush out the larger bodies. If it is desired to flush out the first catheter 20 and a valve 40 is present, the pressure can be sufficient to overcome the valve and through suction induce a flow through the first catheter. Alternatively, the needle can be used to force the valve 40 open to allow this back flow. The reversed flow of fluid can force any large bodies out through the openings 22, 24, clearing the first catheter 20.

The various devices, methods, procedures, and techniques described above provide a number of ways to carry out the invention. Of course, it is to be understood that not necessarily all objectives or advantages described may be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A method of removing excess cerebrospinal fluid, the method comprising:
   receiving cerebrospinal fluid from an intracranial region;
   conveying the cerebrospinal fluid to a chamber mounted at a skull;
   conveying the cerebrospinal fluid from the chamber to a subarachnoid space of the brain when pressure in the subarachnoid space is not excessive; and
   conveying the cerebrospinal fluid from the chamber to a subgaleal pocket when the pressure in the subarachnoid space is excessive,
   wherein the method is performed continuously over at least a week without surgical interference inside the skull.

2. The method of claim 1, further comprising draining the cerebrospinal fluid from the subgaleal pocket.

3. The method of claim 1, further comprising hindering a flow of cerebrospinal fluid back into the intracranial region with a valve.

4. The method of claim 1, wherein the method is performed continuously over at least a month without surgical interference inside the skull.

5. The method of claim 1, wherein the method is performed continuously over at least a year without surgical interference inside the skull.

6. The method of claim 1, further comprising the step of determining that larger bodies have collected inside the chamber.

7. The method of claim 6, further comprising the step of injecting a saline solution into the chamber while mounted at the skull.

8. The method of claim 7, wherein the step of injecting is done through a needle.

9. The method of claim 7, wherein the step of injecting is performed at a pressure sufficient to flush larger bodies out of the chamber.

10. The method of claim 1, further comprising the step of pumping a dome which forms at least a part of the chamber.

11. The method of claim 1, further comprising conveying the cerebrospinal fluid from the chamber to both the subarachnoid space and the subgaleal pocket simultaneously.

* * * * *